United States Patent [19]

Katopodis

[11] Patent Number: 4,701,418
[45] Date of Patent: Oct. 20, 1987

[54] METHOD FOR DETERMINING LIPID BOUND SIALIC ACID IN WHOLE BLOOD

[75] Inventor: Nonda Katopodis, Stamford, Conn.

[73] Assignee: Dianon Systems, Inc., Stratford, Conn.

[21] Appl. No.: 711,592

[22] Filed: Mar. 18, 1985

Related U.S. Application Data

[63] Continuation-in-part of Ser. No. 595,425, Mar. 30, 1984, abandoned.

[51] Int. Cl.$^4$ ............... G01N 33/48; G01N 33/66; G01N 33/92
[52] U.S. Cl. ........................ 436/64; 422/61; 436/93; 436/71; 436/87; 436/164; 436/178
[58] Field of Search ............ 436/63, 64, 71, 87, 436/93, 94, 164, 177, 178, 129; 422/61

[56] References Cited

U.S. PATENT DOCUMENTS

| | | | |
|---|---|---|---|
| 4,115,062 | 9/1978 | Moore et al. | 436/64 |
| 4,342,567 | 8/1982 | Katopodis et al. | 436/164 |
| 4,541,987 | 9/1985 | Guadagno | 422/61 |

OTHER PUBLICATIONS

Kloppel et al., *Proc. Nat'l Acad. Sci.*, U.S.A., vol. 74, No. 7, pp. 3011–3013, 1977.
Albouz et al., Chem. Abstracts, v. 92 (21135b) 1980.
Silver et al., *Cancer Research*, v. 39, pp. 5036–5042, 1979.

*Primary Examiner*—Barry S. Richman
*Assistant Examiner*—C. M. Delahunty
*Attorney, Agent, or Firm*—John P. White

[57] ABSTRACT

The amount of lipid bound sialic acid in a whole blood sample may be determined by a method, which may be automated, involving the following steps: adding to the sample a lower alkyl alcohol and deionized distilled water; mixing the resulting admixture; adding to it a mixture of lower alkyl chlorinated hydrocarbon and a lower alkyl alcohol; treating by mixing and centrifuging the mixture until a recoverable, substantially clear upper phase forms; recovering the upper phase and adding to it a protein-precipitating agent, preferably in admixture with an adsorbing material; mixing the resulting admixture; recovering the resulting precipitate, suspending the precipitate in distilled water and determining the amount of lipid bound sialic acid present. The presently preferred mixture for addition to the upper phase is a mixture of 75% by weight phosphotungstic acid and 25% by weight silica gel on a dry weight basis. By so determining the amount of lipid bound sialic acid present in a whole blood sample and comparing the amount with values obtained for subjects known to have cancer one may diagnose the presence of cancer in a subject. Alternatively, by determining the amount of lipid bound sialic acid present in whole blood samples obtained from a subject over a period of time and comparing each amount so determined with preceding amounts one may monitor the progression, remission or recurrence of cancer in a subject.

46 Claims, No Drawings

METHOD FOR DETERMINING LIPID BOUND SIALIC ACID IN WHOLE BLOOD

This application is a continuation-in-part of U.S. Ser. No. 595,425, filed Mar 30, 1984, now abandoned, the contents of which are hereby incorporated by reference into the present application.

BACKGROUND OF THE INVENTION

This invention concerns a method for the determination of sialic acid, particularly lipid bound sialic acid, in whole blood which provides a number of advantages over existing methods involving blood plasma or sarum, including simplicity, cost, convenience, specificity and sensitivity.

Much work has been done which indicates that elevated sialic acid content in blood sera of a patient is an indication of the presence of cancer.

Thus, for example, U.S. Pat. No. 4,146,603 to Davidson et al. discloses and claims a fairly complex series of procedures whereby elevated sialic acid content is a determinant with respect to cancer specific determinations.

MacBeth and Bekesi, Cancer Res. 22:1170–1176 (1962) measured plasma glycoproteins and found galactose and mannose values were seen in breast cases without metastases. Kloppel et al., Proc. Natl. Acad. Sc, 74:3011—3013 (1977) reported 2.5-fold increases of serum sialic acid glycolipids in mice bearing transplantable mammary carcinomas and 2-fold increases in human carcinoma patients. The method involved column chromatographic separation of the gangliosides. A minimum of 1 ml whole blood was required Kloppel et al., Am. J. Vet. Res. 39:1377–1380 (1978) also reported increases of sialic acid in 92% of 24 dogs; however, a number of false positives were observed in dogs with other disorders. In leukemic AKR/J mice, Lengle, J. Natl. Cancer Inst. 62:1563–1567 (1979) found increased lipid bound sialic acid in their plasma and thymic lymphocytes. Lipid bound sialic acid levels were found increased in plasma and erythrocytes of humans bearing melanomas. Portoukalian et al., Biochem. Biophys. Res. Commun. 85:916–920 (1978). Chromatographic separation and purification on columns was followed by evaluation on chromatoplates. Silver et al., Cancer 41:1497–1499 (1978); Cancer Res. 39:5036–5042 (1979) have reported elevated serum sialic acid values in melanoma patients that were significantly related to the tumor burden. However, 36% of patients with observable tumors showed no elevated serum sialic acid. Hogan-Ryan et al., Br. J. Cancer 41:587–592 (1980) reporting on total bound serum sialic acid in patients with breast cancer found elevations that corresponded with tumor stage.

One specific method over which the present invention is an improvement is disclosed in the American Association for Cancer Research Annual Meeting PROCEEDINGS Vol 21, March 1980, as Abstract No. 728 by Katopdis et al. Briefly, this method requires that a 100 µl plasma sample (reduced to 50 µl) be extracted with 6 ml of a chloroform/methanol mixture (2:1, volume to volume). The lipid extract is then partitioned with 0.2 of its volume of water. The aqueous phase is evaporated to dryness and the residue redissolved in water. The lipid bound sialic acid is then purified by trichloroacetic acid-phosphotungstic acid precipitation and, after the removal of the supernatant from the resultant precipitate, the precipitate is determined by the Svennerhelm and Miettien method (Svennerholm, Quantitative Estimation of Sialic Acid . . , Biochem. Siophys. Acta 24, pp. 604–611 (1957).

The other specific method over which the present invention is an improvement is disclosed in Katopodis and Stock, U.S. Pat. No. 4,342,567. This method is similar to the foregoing but requires only about 50 µl of sample rather than the 100 µl required by the prior art method. The drying step is eliminated and there is no use of trichloroacetic acid. Phosphotungstic acid is used alone. This prior method consists essentially of the following steps:

1. To a screw cap culture tube, 13×100 mm, add 150. distilled water with a 500λ Hamiltion syringe. To this tube transfer a capillary pipette (Unopette, Becton-Dickinson 5841) with its content of 44.7λ of plasma (or serum). Vortex the contents for 5 seconds. Transfer the tube to crushed ice.

2. Add to the tube 3.0 ml cold (4°-5° C.) 2:1 v/v mixture of chloroform and methanol and vortex the mixture for 10 seconds.

3. To this mixture add 0.5 ml cold distilled water, cap the tube and mix the contents by repeatedly inverting the tube for 30 seconds.

4. After centrifuging the tube 5 minutes at room temperature at 2500 rpm, transfer 1 ml of the upper layer into a culture tube like the one already used.

5. Add 50λ phosphotungstic acid solution (1 g/ml) and after mixing let it stand at room temperature for 5 minutes.

6. Centrirage for 5 minutes at 2500 rpm and remove the supernatant by suction.

7. Add 1 ml water and vortex until the precipitate is in suspension without gross particles (about 1 minute).

8. Add 1 ml of the resorcinol reagent, mix and place the tube in boiling water for exactly 15 minutes.

9. Immediately after the 15 minutes, transfer the tube to an ice and water bath and leave for 10 minutes.

10. To the ice cold tube add 2 ml butyl acetate-n-butanol 85:15 v/v mixture at room temperature, vortex and centrifuge for 5 minutes at 2500 rpm.

11. Read the extracted blue color at 580 nm and the amount of lipid bound sialic acid (LSA) is determined by use of a standard curve developed from a standard sample of n-acetyl neuraminic acid (NANA) and use of this formula:

$$\text{LSA (mg/100 ml plasma)} = (x \cdot 100,000\lambda)/(y \cdot 44.7\lambda \cdot 1000)$$

x = γ NANA read from standard curve for the sample
y = 1 ml of supernatant ÷ volume of entire supernatant The preceding method suffers a number of disadvantages including the following: the need for a precisely defined 44.7λ starting sample; the need for the sample to be in the form of plasma rather than whole blood; inconvenience; the increased labor, equipment, expense and likelihood of error associated with converting the sample from blood to plasma; the loss of lipid bound sialic acid during the tube inversion step creating reduced final values; incomplete precipitation of the lipid bound sialic acid with phosphotungstic acid, which is a particular problem when working with samples in which the amount exceeds normal values by only small amounts (e.g., early in cancer development); the 5 minutes' waiting time after phosphotungstic acid addition which limits the rapidity of the test and the undesirably high cost of the test.

Using the preceding method different laboratories have obtained results which vary widely. Table I sets forth results obtained by others and illustrates the variability obtained when samples from normal subjects were tested.

TABLE I

RESULTS OBTAINED BY DIFFERENT LABORATORIES USING THE METHOD OF U.S. Pat. No. 4,342,567

NORMAL SAMPLES

| RANGE mgs % | MEAN mgs % | UPPER LIMIT mgs % | |
|---|---|---|---|
| 15.0–20.0 | 17.5 | 20.0 | (1) |
| 12.8–16.8 | 14.8 | 16.8 | (2) |
| 11.6–19.7 | 15.7 | 19.7 | (3) |
| 11.6–19.1 | 15.4 | 19.1 | (4) |
| 15.0–25.0 | 20.0 | 25.0 | (5) |
| 11.1–15.7 | 13.4 | 15.7 | (6) |
| 16.4–26.6 | 21.5 | 26.6 | (7) |
| NO INFO | 15.3 | NO INFO | (8) |
| NO INFO | NO INFO | 17.2 | (9) |
| 12.6–17.2 | 14.9 | 17.2 | (10) |
| 11.9–26.2 | 19.1 | 26.2 | (11) |
| 15.5–22.5 | 19.0 | 22.5 | (12) |
| 8.7–18.5 | 13.6 | 18.5 | (13) |
| 10.9–18.9 | 14.9 | 18.9 | (14) |
| 10.0–21.0 | 15.5 | 21.0 | (15) |
| MEAN- 12.3–20.6 | 16.4 | 18.2 | |

(1) KATOPODIS AND STOCK, U.S. Pat. No. 4,342,567
(2) CHEN SHU-PAN et al., J. SHANGHAI MED. VOL. 6, 1983
(3) A. M. DNISTRIAN et al., CLINICAL CHEM. 27(10) 1981
(4) S. KAKARI et al., ANTICANCER RES. 4, Suppl. 1:3-6, 1984
(5) L. SANTAMARIA et al., MED. BIOLOGIE ENVIR. VOL. 12 1984
(6) A. M. DNISTRIAN et al., AACR VOL. 23, 609, 1982
(7) P. KOSMIDIS et al., ASCO, VOL. 2, C-1, 1983
(8) D. MUNJAL et al., FED. PROC., VOL. 42(3), March 1983
(9) K. M. ERBIL et al., CL. CHEM. 29, VOL. 6(194), 1983
(10) CHEN SHU-PAN et al., CHIN. J. OBSTET. & GYN. 18(4):235-38 1983
(11) L. SALVAGNO et al., 13 INTL. CONG. OF CHEMO., 1983 (VIENNA)
(12) L. SALVAGNO et al., I. OF CANCER RESEARCH, 1983
(13) A. K. BHARGAVA et al., ASCO, VOL. 6, No. 2, 1984
(14) S. KAKARI et al., INTL. MEETINGS, SALONICA, GREECE, 1982
(15) T. WUSTROW, GERMAN CANCER CONGRESS, 25/6 GL 1983

SUMMARY OF THE INVENTION

In a preferred embodiment, this invention provides a method for determining the amount of lipid bound sialic acid in a sample of human whole blood involving the following steps:

(a) adding to a predetermined volume of a whole blood sample a lower alkyl alcohol and deionized distilled water, the combined volume added being about thirty times the predetermined volume of the whole blood sample, and the volume ratio of lower alkyl alcohol to water added being about 2:1;

(b) mixing the diluted sample for a suitable period of time to obtain a substantially homogeneous sample;

(c) adding to the resulting sample a mixture of chloroform and a lower alkyl alcohol, the volume of the mixture added being about forty times the predetermined volume of the whole blood sample, and the volume ratio of chloroform to alcohol in the mixture being about 10:1;

(d) treating the resulting admixture for a suitable period of time to dissolve matter present in the sample in the chloroform/alcohol mixture and to permit formation of a recoverable, substantially clear upper phase;

(e) separately recovering from the clear upper phase so formed a predetermined volume of the upper phase;

(f) adding to the predetermined volume of the upper phase an amount of a protein-precipitating agent effective to cause precipitation of the lipid bound sialic acid;

(g) mixing the resulting admixture;

(h) separately recovering the resulting precipitate;

(i) suspending the precipitate in a suitable volume of distilled water; and (j) determining the amount of lipid bound sialic acid present in the suspended precipitate and thereby the amount present in the whole blood sample.

This invention also provides a method for determining the amount of sialic acid in a sample of human whole blood which comprises the following steps:

(a) adding to a predetermined volume of a whole blood sample a sufficient combined volume of a lower alkyl alcohol and deionized distilled water to disrupt the blood cells present in the sample and to effect substantially complete dissociation of cell membrane material, the ratio of lower alkyl alcohol to water added being such that agglomeration of material in the sample is avoided;

(b) mixing the resulting sample for a suitable period of time to obtain a substantially homogeneous sample;

(c) adding to the mixed sample a sufficient volume of a mixture of a lower alkyl alcohol and a chlorinated lower alkyl hydrocarbon to extract sialic acid-containing material present in the mixed sample, the ratio of total lower alkyl alcohol added in this step (c) and in step (a) to chlorinated lower alkyl hydrocarbon being such that agglomeration of material in the sample is avoided;

(d) treating the resulting admixture for a suitable period of time to dissolve sialic acid-containing material present in the sample in the chlorinated hydrocarbon/methanol/water admixture and to permit formation of a recoverable, substantially clear upper phase;

(e) separately recovering from the clear upper phase so formed a predetermined volume of the upper phase;

(f) adding to the predetermined volume of the upper phase an amount of a protein-precipitating agent effective to cause precipitation of sialic acid-containing material present in the upper phase;

(g) mixing the resulting admixture;

(h) separately recovering the resulting precipitate;

(i) suspending the precipitate in a suitable volume of distilled water; and (j) determining the amount of sialic acid present in the suspended precipitate and thereby the amount present in the whole blood sample.

Furthermore, this invention provides a method for determining the amount of lipid bound sialic acid in a sample of human whole blood which comprises the following steps:

(a) adding to a predetermined volume of a whole blood sample a lower alkyl alcohol and deionized distilled water to disrupt the blood cells present in the sample and to effect substantially complete dissociation of cell membrane material, the combined volume added being about 20 to 50 times the predetermined volume of the whole blood sample, and the volume ratio of lower alkyl alcohol to water added being in the range from about 3:1 to about 1:1;

(b) mixing the diluted sample for a suitable period of time to obtain a substantially homogeneous sample;

(c) adding to the mixed sample a mixture of a lower alkyl alcohol and a chlorinated lower alkyl hydrocarbon to extract sialic acid-containing material present in the mixed sample, the volume of the mixture added being about 20 to 60 times the predetermined volume of the whole blood sample, and the volume ratio of chlorinated lower alkyl hydrocarbon to lower alkyl alcohol in the mixture being in the range from about 15:1 to about 3:1;

(d) treating the resulting admixture for a suitable period of time to dissolve sialic acid-containing material present in the sample in the chlorinated hydrocarbon/lower alkyl alcohol/water admixture and to permit formation of a recoverable, substantially clear upper phase;

(e) separately recovering from the clear upper phase so formed a predetermined volume of the upper phase;

(f) adding to the predetermined volume of the upper phase an amount of a protein-precipitating agent effective to cause precipitation of the lipid bound sialic acid;

(g) mixing the resulting admixture;

(h) separately recovering from the mixed admixture the resulting precipitate;

(i) suspending the precipitate in a suitable volume of distilled water; and (j) determining the amount of lipid bound sialic acid present in the suspended precipitate and thereby the amount present in the whole blood sample.

The preferred mixture for effecting precipitation of lipid bound sialic acid is one which comprises about 75% by weight phosphotungstic acid and about 25% by weight silica gel.

Desirably, the blood to be tested in adsorbed to and dried on a suitable support, e.g., a filter paper strip or circle, onto which the sample has been dried, or the blood has been dried in a suitable container, e.g., a test tube or glass slide. In such cases the sample is first treated with deionized distilled water before the amount of sialic acid or lipid bound sialic acid present in the sample is determined.

This invention also provides a method and kit for diagnosing cancer in a human subject which comprises determining the amount of lipid bound sialic acid in a sample of a subject's blood and comparing the amount so obtained with values obtained for subjects known to have cancer or with values obtained for the same subject over a period of time.

DETAILED DESCRIPTION OF THE INVENTION

The amount of lipid bound sialic acid in a sample of human whole blood may be determined and the amount so determined used as a diagnostic indicator of cancer. A preliminary step to the method is to obtain a sample to be tested. The sample will typically be recovered from a subject and treated using methods described hereinafter. The blood may be employed directly and may be maintained at a proper storage temperature, e.g. below about 4° C., during transport or storage by packing the sample in an insulated container with dry ice, or more economically, with a commercially available freeze pack. Preferably, however, the sample is placed on a suitable support and dried; and then the sample-bearing support employed in the test by first redissolving the dried sample at the beginning of the assay described hereinafter. Suitable support materials include any adsorbent, bibulous or porous material on which the sample can spread and dry, and which does not interfere with the assay, e.g. which does not, under assay conditions, dissolve in or react with solvents, e.g. methanol or aqueous methanol, with which the support material is contacted during the assay. Numerous support materials known in the blood assay art which meet these criteria may be used, e.g. natural or synthetic cellulosic materials such as paper or nitrocellulose in a variety of forms such as a paper strip or circle of compressed cellulosic material. Numerous types of paper strips or circles may be utilized such as filter paper, chromatography paper or specimen collection paper. Examples of such include Whatman Grade 54 and #903 TM available from Schleicher & Schuel, Keene, N.H. Compressed cellulose substances include Whatman Accelerators #1702.005. Also suitable are fibrous materials such as glass, natural cloth, e.g. cotton, and synthetic materials such as tetlon, nylon and polyolefins, e.g. polyethylene and polypropylene. In the case of glass or synthetic materials, non-fibrous fabricated forms may also be used such as sintered, fritted or otherwise porous strips, circles, etc. Samples may also be dried on the inner surface of a test tube or other suitable sample container. Additionally, suitable support materials may also be used in the form of an adsorbent powder packaged in a vial or tube. The use of whole blood samples dried on such supports provides major advantages over plasma per se in terms of sample stability, transportation and storage and makes it possible to perform the method of the present invention on samples drawn from patients located at great distances from the actual testing site. Samples prepared on such support materials may be maintained at room temperature for up to one week, e.g. during shipping or storage, with no significant change in lipid bound sialic acid concentration. In a preferred embodiment, the paper strip is impregnated with an agent which improves the sample's stability, e.g., a pH 7-8 $NaHCO_3$ solution, or a 1% (w/v) sodium azide solution, or a 0.01-1.0% (w/v) benzamidine hydrochloride solution or a 0.001-0.01% (w/v) phenylmethylsulfonyl fluoride solution. In addition, standard known samples may be prepared by any of the previously mentioned methods.

The initial step of the method of the present invention is to add to a predetermined volume of a whole blood sample a lower alkyl alcohol, e.g., methanol, and deionized distilled water, the combined volume added being about twenty to fifty times, e.g. about thirty times, the predetermined volume of the whole blood sample, and the volume ratio of alcohol to water added being about 2:1. Thus, if the initial blood sample is 50 $\mu l$ in a small tube or container, the combined amount added may be about 1.5 ml. In embodiments wherein the initial sample has been dried onto paper or another suitable support, the paper or other support is treated by addition of about 0.5 ml of deionized distilled water, followed by addition of about 1.0 ml or methanol.

The diluted sample is mixed, e.g., by gentle interrupted vortexing, for a suitable time to obtain a substantially homogeneous sample, e.g., at least 20 seconds, preferably by vortexing gently for at least 10 seconds and more preferably by vortexing gently for at least 10 seconds with three interruptions followed by at least 10 additional seconds with three interruptions. A mixture of a chlorinated lower alkyl hydrocarbon and a lower alkyl alcohol in which the volume ratio of chlorinated lower alkyl hydrocarbon to alcohol is from about 15 to 1 to about 5 to 1, e.g., about 10 to 1, is then added to the mixed sample. The volume of the chlorinated hydrocarbon and alcohol mixture added is about 20 to 60 times, e.g., about forty times the original, i.e. predetermined, volume of the whole blood sample. Thus, if the original sample volume is 50 $\mu l$, the volume of mixture added is 2 μl. Suitable chlorinated hydrocarbons include chloroform, methylene chloride, ethylene chloride, propylene chloride and carbon tetrachloride, chloroform being presently preferred. The lower alkyl alcohol may be methanol, ethanol, propanol, n.butanol, isopropanol, isobutanol or isoamyl alcohol. However, the greater the number of carbon atoms in the alcohol, the less effective the mixture is in terms of lipid bound stalic acid extraction as opposed to total sialic acid extraction. Stated differently, the greater the number of carbon atoms in the alcohol, the greater the amount of sialic acid which is not lipid bound which is precipitated. Therefore, the preferred alcohol is methanol since the other alcohols extract higher amounts of total sialic acid, i.e., lipid bound plus unbound sialic acid, and other contaminants and therefore reduce the diagnostic value of the test.

The resulting admixture is then treated, first by mixing for a suitable period of time to dissolve matter present in the sample in the chloroform/alcohol mixture and to permit formation of a substantially clear upper phase, e.g., by gentle interrupted vortexing for at least 20 seconds followed by centrifugation at above 2000 rpm (750 g) for at least 2 minutes, more preferably the vortexing being for at least 10 seconds with three interruptions followed by at least 10 additional seconds with three interruptions.

A predetermined volume of the upper phase is then separately recovered from the clear upper phase so formed, preferably by removing the upper phase from the lower phase and discarding the latter. The predetermined volume separately recovered will depend upon the convenience of removing a large volume of the upper phase without disturbing the interface or other material in the tube. Thus, if the original, i.e. predetermined, blood volume is about 50 μl, the preferred volume of upper phase separately recovered will be about 0.8 ml.

To the predetermined volume of the upper phase there is added an amount of a protein-precipitating agent, either alone or preferably in admixture with an adsorbing material, the amount of the former being effective to cause precipitation or the lipid bound sialic acid and the amount of the latter being effective to adsorb the precipitated lipid bound sialic acid. Suitable protein-precipitating agents include phosphorungstic acid, trichloroacetic acid, ammonium sulfate (e.g., saturated pH 4.0-6.0 buffered solution) or mixtures thereof (e.g., 90 by weight phosphortungstic acid; 10% by weight trichloroacetic acid). Suitable adsorbing materials include siliceous materials such as silica and silica gel and aluminum oxide, with or without additional binder materials. If a mixture of protein-precipitating agent and absorbing material is employed, the relative amount by dry weight of the former to the latter is about 3:1. The presently preferred mixture contains about 5% by weight phosphotangstic acid and 26% by weight silica gel and the amount added is about 60-80 mgs per 0.8 ml of upper phase in the form of a powder or pellet. The presently preferred silica gels are available from MCB Manufacturing Chemists, Inc., Grades 950 and 62 (60-200 mesh). Another preferred mixture contains about 25% by weight $Al_2O_3$ (Florisil ®—30-60 mesh) in place of silica gel.

The resulting admixture is then mixed, e.g., by vortexing briefly (at least 3 seconds), and the resulting precipitate is recovered; e.g., by centrifugation for at least 3 minutes at a speed about 2000 rpm and discarding the supernatant. The precipitate is then suspended in a suitable volume of distilled water for convenient handling, e.g., about 1 ml, and the amount of lipid bound sialic acid present in the suspended precipitate and thereby the amount present in the blood sample is determined. More specifically, the amount of lipid bound sialic acid is determined by adding to the suspended precipitate a suitable volume, e.g., 1 ml, of resorcinol reagent, mixing, boiling for 15 minutes, cooling for at least about 10 minutes in an ice bath, centrifuging for at least 2 minutes at about 2000 rpm, adding about twice said suitable volume, e.g., 2 mls, of a mixture of butyl acetate and n-butanol (35:15 v/v;, mixing, centrifuging for at least 5 minutes at above about 2000 rpm, separating the organic layer, reading at 580 nm the extracted blue color present in the organic layer, determining the amount of lipid bound sialic acid using standard curves developed from a known sample of n-acetyl neuraminic acid (NANA) under the same conditions and applying the formula:

LSA (mg/100 ml whole blood)=$(x\cdot10^5\mu l)/(y\cdot z\mu l\cdot1000)$ where x=λ NANA read from standard curve, y=the volume of upper phase recovered ÷ volume of entire upper phase and z=the predetermined volume, e.g. 50 μl, of the whole blood sample.

The various steps of sample handling and manipulation in the various embodiments of this invention, e.g. addition of reagents, mixing, recovering aliquot volumes, centrifuging, etc., may be automated, e.g. with a suitably programmed robotic device(s) appropriately interfaced with suitable equipment for effecting the manipulations, e.g. syringes, delivery tubes, centrifuge, vortexer or other mixing apparatus, etc. Similarly the absorbance of light due to the presence of sialic acid may be detected automatically with an appropriately programmed detection apparatus, e.g. a spectrophotometer, suitably interfaced with the robotic device(s). Likewise, the amount of lipid bound sialic acid may be calculated directly from the absorbance so detected using a suitably programmed computer, e.g. microcomputer, appropriately interfaced with the detection device. By automating the method as described above, a reduction in cost per assay and an improvement in the coefficient of variation for the assay may be achieved.

This invention also provides a method of diagnosing cancer in a human subject which comprises determining the amount of lipid bound sialic acid in a sample or the subject's blood according to the method described herein and comparing the amount so determined with values obtained for subjects known to have cancer, or alternatively comparing the amount so determined with values obtained over a period of time for the same subject.

Furthermore, this invention provides a cancer diagnostic kit comprising suitable fibrous or other support means e.g., paper strips or circles for the sample to be tested, preferably impregnated with a stabilizing agent; fibrous or other support means e.g., paper strips or circles onto which known amounts of reference samples and n-acetyl neuraminic acid standards have been dried; a container of a mixture of lower alkyl alcohol, e.g., methanol and deionized distilled water in a 2:1 volume ratio; a container of a mixture of chlorinated lower alkyl hydrocarbon, e.g., chloroform and lower alkyl alcohol, e.g., methanol in a 10:1 volume ratio a container of (10:1 v/v); protein precipitating agent, alone or in admixture with adsorbing material; a container of resorcinol reagent; a container of a mixture of butylacetate and n-butanol in an 85:15 volume, ratio a container of a deionized distilled water and pipette tips for the sample.

In addition to the preceding preferred embodiment, this invention provides the first methods for determining the amount of sialic acid and lipid bound sialic acid in human whole blood. The method for determining the amount of sialic acid in a sample of human blood involves the following steps:

(a) adding to a predetermined volume of a blood sample a sufficient combined volume of a lower alkyl alcohol, e.g., methanol, and deionized distilled water to disrupt blood cells present in the sample and to effect substantially complete dissociation of cell membrane material, the combined volume added being about 50 to 10 times, e.g. 30 times, the predetermined volume of the blood sample, and the ratio of lower alkyl alcohol to water added being such that agglomeration of material in the sample is avoided;

(b) mixing the resulting sample for a suitable period of time to obtain a substantially homogeneous sample;

(c) adding to the resulting sample a sufficient volume of a mixture of chlorinated lower alkyl hydrocarbon, e.g., chloroform, and lower alkyl alcohol, e.g., methanol, to extract sialic acid present in the mixed sample, the volume of the mixture added being about 60 to 20 times, e.g. 40 times, the predetermined volume of the blood sample, and the ratio of total chlorinated hydrocarbon in this step (c) and in step (a) to alcohol being such that agglomeration of material in the sample is avoided; and (d) treating the resulting admixture in the same manner as described hereinabove in the preferred method.

The method for determining the amount of lipid bound sialic acid in a sample of human whole blood involves the following steps:

(a) adding to a predetermined volume of a blood sample a lower alkyl alcohol, e.g., methanol, and deionized distilled water in a sufficient combined volume, such as 50 to 10 times, e.g. 30 times the predetermined volume of the blood sample, to disrupt blood cells present in the sample and to effect substantially complete dissociation of cell membrane material, the volume ratio of lower alkyl alcohol to water added being in the range from about 3:1 to about 1:1, e.g., about 2:1;

(b) mixing the resulting sample for a suitable period of time to obtain a substantially homogeneous sample;

(c) adding to the resulting sample a mixture of chlorinated lower alkyl hydrocarbon, e.g. chloroform, and lower alkyl alcohol, e.g., methanol, the volume of the mixture added being a sufficient volume such as 60 to 20 times, e.g. 40 times, the predetermined volume of the blood sample to extract sialic acid present in the mixed sample, the volume ratio of chlorinated lower alkyl hydrocarbon to lower alkyl alcohol being in the range from about 15:1 to about 5:1, e.g., about 10:1; and (d) treating the resulting admixture in the same manner as described hereinabove in the preferred method.

The examples which follow are set forth to aid in an understanding of the invention but are not intended to, and should not be construed to, limit in any way the invention as set forth in the claims which follow thereafter.

EXAMPLES

EXAMPLE 1

BLOOD COLLECTION AND STORAGE

Whole blood is collected in a vacutainer (purple cap) with liquid EDTA (Venoject lavender stopper tubes, which contain 15% EDTA) or microtainer with EDTA coated beads. Aliquots of the collected blood are either stored at $-20°$ C. for several months before analysis or analyzed fresh. In either case the blood is placed on crushed ice prior to analysis.

EXAMPLE 2

DETERMINATION OF LIPID BOUND SIALIC ACID (LSA) IN A 50 $\mu$L BLOOD SAMPLE

50 $\mu$l of a sample of blood collected in accordance with Example 1 is placed in a suitable tube or container, e.g., a screw cap culture tube (13×100 mm). 1.5 ml of a mixture of 100 ml absolute methanol and 50 ml deionized distilled water, pH 5-6, is added, the resulting mixture is vortexed (Vortex-genie(r), Scientific Industries, Inc.) for 10 seconds with three interruptions and then again for an additional 10 seconds with three interruptions for a total vortexing time of 20 seconds. 2 ml of a 10:1 volume ratio mixture of chloroform and methanol is then added. Chloroform, methanol and other solvents were obtained in Analytical Reagent (AR) grade from Mallinckrodt, Inc. The mixture is vortexed for 10 seconds with three interruptions and then again for an additional 10 seconds with three interruptions for a total vortexing time of 20 seconds. The sample is next centrifuged for 5 minutes at a speed above 2000 rpm (Model IECHN-SII Centrifuge, Damon/International Equipment Co., with an IEC #958 6-position rotor). 0.8 ml of the resulting upper phase is transferred to a separate tube and 60-80 mg of a mixture of 75% phosphotungatic acid (AR grade, Sigma) and 25% silica gel (60F254 MCB Manufacturing Chemists, Inc.) on a dry weight basis is added in the form of a dried powder or pellet. The resulting sample is then vortexed briefly and centrifuged for 5 minutes at a speed above 2000 rpm. The supernatant is removed, preferably by suction or decanting to avoid disturbing the precipitate, and discarded. The resulting sample is then vortexed briefly and 1 ml of distilled water is added and brief vortexing again performed to suspend the precipitate. 1 ml of resorcinol reagent at 0°-4° C. is then added. The sample is vortexed and then placed in boiling water for 15 minutes. Immediately after boiling, the sample is placed in an ice and water bath for 5 minutes. Thereafter, the cold tube is centrifuged for 1 to 2 minutes at a speed above 2000 rpm. 2 ml of butylacetate and butanol mixture (85:15 v/v) is added, and the sample vortexed and centrifuged for 5 minutes at a speed above 2000 rpm. The extracted blue color is then read at 580 nm (Model 34 spectrophotometer, Deckman Instruments, Inc.) and the amount of lipid bound sialic acid determined by use of a standard curve developed from a standard sample of n-acetyl neuraminic acid using the formula:

$$\text{LSA (mg/100 ml whole blood)} = (x \cdot 10^5 \mu l)/(y \cdot z \mu l \cdot 1000)$$

where x=YNANA read from standard curve, y=0.8 ml of upper phase recovered ÷ volume of entire upper phase and z =50 $\mu$l, the predetermined volume of the whole blood sample.

EXAMPLE 3
USE OF PAPER STRIP

Plasma collection paper (Schleicher & Schuell #903) in a strip 1.0×0.5 cm is used. 50 μl of blood is loaded onto the strip with a pipetter and a tip. The strip is dried in the air for 3 minutes and cut into small pieces with scissors at the time it is placed into the analysis tube. The tube is then covered and kept at room temperature until further processing. To the tube with the cut-up strips add 0.5 ml of deionized distilled water followed by 1.0 ml of absolute methanol and then proceed with the procedure as described in Example 2.

EXAMPLE 4
PREPARATION OF IMPREGNATED PAPER

A 0.1% solution of sodium azide (Fisher, 316MA, purified) in water is prepared. 50 μl of this solution is applied to a 1.5×1.0 cm strip of filter paper (Schleicher & Schuell #903). The strip is dried under a stream of hot air. To this strip 50 μl of whole blood is applied and the blood dried prior to analysis. The strip may be stored for a substantial period of time at room temperature prior to analysis.

EXAMPLE 5
RESORCINOL REAGENT

1. Stock Resorcinol solution (2%)

In a 100 ml volumetric flask weigh out 2 grams of resorcinol (SIGMA #R-1000). Fill up to the mark with distilled water. Keep the solution refrigerated in a dark bottle.

2. Cupric sulfate 0.1 M ($CaSO_4 \cdot 5H_2O$ MALLINCKRODT #4844)

In a 100 ml volumetric flask weigh out 2.497 gm of $CuSO_4 \cdot 5H_2O$. Fill up to the mark with distilled water.

3. HCl conc. FISHER Co. #A-144

Preparation of Resorcinol Reagent:
In a 100 ml volumetric flask add:
(a) 10 ml of 2% stock resorcinol solution
(b) 0.25 ml of 0.1 M $CuSO_4$ (Mix)
(c) 9.75 ml distilled water (Mix)
(d) fill up to the mark with HCl.

Mix, transfer to dark container and store at 0°–5° C.

EXAMPLE 6
PREPARATION OF REFERENCE SAMPLE

A paper strip (Schleicher & Schuell #903) is used for the absorption of 50 μl of a sample of known LSA concentration. The strip (1.0×0.5 cm) is dried in the air for 5 minutes and then cut into small pieces at the time it is placed into the analysis tube. The tube is covered until the time for analysis at which point the procedure described in Example 2 is followed.

EXAMPLE 7
STANDARD NANA CURVE CONSTRUCTION

N-acetyl neuraminic acid (98% SIGMA) is used for the standard NANA solution at a concentration of 1 mg/ml. The same types of filter paper and procedures are used to construct the standard curve except that instead of using 50 μl of plasma 5, 10 and 15 μl of the standard NANA solution is employed. The same procedures are employed as described in Example 2 for determining LSA content and a linear standard curve constructed which can be used as a reference for comparison with the values determined using the method of present invention.

EXAMPLE 8

Table II sets forth a comparison of the results obtained when lipid bound sialic acid values were determined for normal and cancer plasma and blood samples using the procedure described in U.S. Pat. No. 4,342,567 and the procedure of the present invention, respectively. Table II indicates that the method of this invention is less affected by contaminants than the prior method, thus reducing the number of false positive readings and providing increased specificity. Table II also indicates that the subject method extracts more LSA (intracellular) thus providing increased sensitivity. These advantages are, of course, independent of the advantages achieved by the method in terms of ease of use and reproducibility of results.

TABLE II
COMPARISON OF LSA VALUES OBTAINED BY THE PREVIOUS PROCEDURE AND THE PROCEDURE OF THIS INVENTION ON NORMAL AND CANCER PLASMA AND BLOOD SAMPLES, RESPECTIVELY

| | PLASMA LSA mgs %[1] | | | WHOLE BLOOD LSA mgs % | |
|---|---|---|---|---|---|
| ALIQUOT | NORMAL | CANCER | ALIQUOT | NORMAL | CANCER |
| 1 | 19.3 | 30.9 | 1 | 19.7 | 33.2 |
| 2 | 18.3 | 26.4 | 2 | 19.0 | 26.0 |
| 3 | 16.4 | 41.7 | 3 | 16.4 | 40.7 |
| 4 | 16.9 | 21.1 | 4 | 17.5 | 24.2 |
| 5 | 20.4 | 20.9 | 5 | 18.9 | 22.0 |
| 6 | 17.9 | 22.0 | 6 | 19.0 | 22.9 |
| 7 | 19.8 | 33.0 | 7 | 17.9 | 31.1 |
| 8 | 20.9 | 32.1 | 8 | 19.7 | 35.1 |
| 9 | 14.5 | 56.0 | 9 | 14.0 | 60.8 |
| 10 | 17.0 | 40.9 | 10 | 16.1 | 46.7 |

[1]U.S. Pat. No. 4,342,567

What is claimed is:

1. A method for extracting lipid bound sialic acid from whole blood and determining the amount of sialic acid in a sample of human whole blood which comprises the following steps:
    (a) adding to a predetermined volume of a whole blood sample a sufficient combined volume of a lower alkyl alcohol and deionized distilled water to disrupt the blood cells present in the sample and to effect substantially complete dissociation of cell membrane material, the ratio of lower alkyl, alcohol to water added being such that agglomeration of said cell membrane material in the sample is avoided;
    (b) mixing the resulting sample for a suitable period of time to obtain a substantially homogeneous sample;
    (c) adding to the mixed sample a sufficient volume of a mixture of a lower alkyl alcohol and a chlorinated lower alkyl hydrocarbon to extract sialic acid-containing material present in the mixed sample, the ratio of total lower alkyl alcohol added in this step (c) and in step (a) to chlorinated lower alkyl hydrocarbon being such that agglomeration of said cell membrane material in the sample is avoided;
    (d) mixing the resulting admixture for a suitable period of time to dissolve sialic acid-containing material present in the sample in the chlorinated hydrocarbon/lower alkyl alcohol/water admixture and to permit formation of a recoverable, substantially clear upper phase;

(e) separately recovering from the clear upper phase so formed a predetermined volume of the upper phase;

(f) adding to the predetermined volume of the upper phase an amount of a protein-precipitating agent effective to cause precipitation of sialic acid-containing materials present in the upper phase;

(g) mixing the resulting admixture;

(h) separately recovering the resulting precipitate;

(i) suspending the precipitate in a suitable volume of distilled water; and (j) determining the amount of sialic acid present in the suspended precipitate and thereby the amount present in the blood sample.

2. A method according to claim 1, wherein in step (a) the blood sample to be tested is dried onto a support means.

3. A method according to claim 2, wherein the support means is a filter paper strip or circle.

4. A method according to claim 2, wherein in step the addition of the deionized distilled water precedes the addition of the lower alkyl alcohol.

5. A method according to claim 2, wherein the support means onto which the blood is dried has previously been impregnated with a stabilizing agent.

6. A method according to claim 5, wherein the stabilizing agent is selected from the group consisting of a pH 7–8 NaHCO$_3$ solution, a 1% (w/v) sodium azide solution, a 0.01–1.0% (w/v) benzamidine hydrochloride solution and a 0.001–0.01% (w/v) phenylmethylsulfonyl fluoride solution.

7. A method for extracting lipid bound sialic acid from whole blood and determining the amount of lipid bound sialic acid in a sample of human whole blood which comprises the following steps;

(a) adding to a predetermined volume of a whole blood sample a lower alkyl alcohol and deionized distilled water in a combined volume of about 20 to 50 times the predetermined volume of the blood sample, to disrupt the blood cells present in the sample and to effect substantially complete dissociation of cell membrane material, the volume ratio of lower alkyl alcohol to water added being in the range from about 3:1 to about 1:1;

(b) mixing the diluted sample for a suitable period of time to obtain a substantially homogeneous sample;

(c) adding to the mixed sample a mixture of a lower alkyl alcohol and a chlorinated lower alkyl hydrocarbon to extract sialic acid present in the mixed sample, the volume of the mixture added being about 20 to 60 times the predetermined volume of the blood sample, and the volume ratio of chlorinated lower alkyl hydrocarbon to lower alkyl alcohol being in the range from about 15:1 to about 5:1;

(d) mixing the resulting admixture for a suitable period of time to dissolve sialic acid present in the sample in the chlorianted hydrocarbon/methanol/water admixture and to permit formation of a recoverable, substantially clear upper phase;

(e) separately recovering from the clear upper phase so formed a predetermined volume of the upper phase;

(f) adding to the predetermined volume of the upper phase an amount of a protein-precipitating agent effective to cause precipitation of the lipid bound sialic acid, (g) mixing the resulting admixture;

(h) separately recovering from the mixed admixture the resulting precipitate;

(i) suspending the precipitate in a suitable volume of deionized distilled water; and (j) determining the amount of lipid bound sialic acid present in the suspended precipitate and thereby the amount present in the blood sample.

8. A method according to claim 7, wherein in step (a) the blood sample to be tested is dried onto a support means.

9. A method according to claim 8, wherein the support means is a filter paper strip or circle.

10. A method according to claim 8, wherein in step the addition of the deionized distilled water precedes the addition of the lower alkyl alcohol.

11. A method according to claim 8, wherein the support means onto which the blood is dried has previously been impregnated with a stabilizing agent.

12. A method according to claim 11, wherein the stabilizing agent is selected from the group consisting of a pH 7–8 NaHCO$_3$ solution, a 1% (w/v) sodium azide solution, a 0.01–1.0% (w/v) benzamidine hydrochloride solution and a 0.001–0.01% (w/v) phenylmethylsulfonyl fluoride solution.

13. A method for extracting lipid bound sialic acid from whole blood and determining the amount of lipid bound sialic acid in a sample of human whole blood which comprises the following steps;

(a) adding to a predetermined volume of a whole blood sample a lower alkyl alcohol and deionized distilled water, the combined volume added being about thirty times the predetermined volume of the whole blood sample, and the volume ratio of alcohol to water added being about 2:1;

(b) mixing the diluted sample for a suitable period of time to obtain a substantially homogeneous sample;

(c) adding to the resulting sample a mixture of a chlorinated lower alkyl hydrocarbon and a lower alkyl alcohol, the volume of the mixture added being about forty times the predetermined volume of the whole blood sample, and the total volume ratio of chlorinated hydrocarbon to alcohol in the mixture being about 10:1;

(d) mixing the resulting admixture for a suitable period of time to dissolve sialic acid containing material present in the sample in the chlorinated hydrocarbon/alcohol mixture and to permit formation of a recoverable, substantially clear upper phase;

(e) separately recovering from the clear upper phase so formed a predetermined volume of the upper phase;

(f) adding to the predetermined volume of the upper phase an amount of a protein-precipitating agent effective to cause precipitation of the lipid bound sialic acid;

(g) mixing the resulting admixture;

(h) separately recovering the resulting precipitate;

(i) suspending the precipitate in a suitable volume of distilled water; and (j) determining the amount of lipid bound sialic acid present in the suspended precipitate and thereby the amount present in the blood sample.

14. A method according to claim 13, wherein in step (b) the mixing comprises gentle interrupted vortexing for at least 20 seconds.

15. A method according to claim 13, wherein in steps (a) and (c) the lower alkyl alcohol is methanol, ethanol, propanol, n-butanol, isopropanol, isobutanol or isoamyl alcohol.

16. A method according to claim 17, wherein in step (c) the chlorinated lower alkyl hydrocarbon is chloroform, methylene chloride, ethylene chloride, propylene chloride or carbon tetrachloride.

17. A method according to claim 13, wherein in step (d) the mixing comprises gentle interrupted vortexing for about 20 seconds followed by centrifuging at above about 2000 rpm for at least 2 minutes.

18. A method according to claim 13, wherein in step (e) the separately recovering comprises removing the upper phase from the lower phase.

19. A method according to claim 13, wherein in step (g) the mixing comprises vortexing for at least 3 seconds.

20. A method according to claim 13, wherein in step (h) the separately recovering comprises centrifuging for at least 3 minutes at a speed above about 2000 rpm.

21. A method according to claim 13, wherein in step (i) the suitable volume is about 1 ml.

22. A method of diagnosing cancer in a human subject which comprises determining the amount of lipid bound sialic acid in a sample of the subject's blood according to the method of claim 13 and comparing the amount so determined with values obtained for subjects known to have cancer.

23. A method of diagnosing cancer in a human subject which comprises determining at regular time intervals the amount of lipid bound sialic acid in a sample of the subject's blood according to the method of claim 13 and comparing the amounts so determined with amounts previously obtained for the subject.

24. A method according to claim 13, wherein in step (f) an absorbing material capable of absorbing precipitated, lipid bound sialic acid is added together with the protein precipitating agent.

25. A method according to claim 24, wherein the adsorbing material is silica gel, silica or aluminum oxide.

26. A method according to claim 13, wherein in step (j) the amount of lipid bound sialic acid is determined by adding to the suspended precipitate a suitable volume of resorcinol reagent, mixing, boiling for 15 minutes, cooling for about 10 minutes in an ice bath, centrifuging for at least 2 minutes at above about 2000 rpm, adding in a volume about twice said suitable volume of resorcinol reagent a mixture of butyl acetate and n-butanol (65:15 v/v), mixing, centrifuging for about 5 minutes at above about 2000 rpm, separating the organic layer, reading at 580 nm the extracted blue color present in the organic layer, determining the amount of lipid bound sialic acid using standard curves developed from a known sample of n-acetyl neuraminic acid (NANA) under the same conditions and applying the formula:

LSA (mg/100 ml whole blood) = $(x \cdot 10^5 \mu l)/(y \cdot z \mu l \cdot 1000)$ where $x = \gamma$NANA read from standard curve, $y$ = volume of upper phase recovered ÷ volume of entire upper phase and $z$ = the predetermined volume of the whole blood sample.

27. A method according to claim 26, wherein the suitable volume of resorcinol reagent is about 1 ml.

28. A method according to claim 13, wherein in step (f) the protein-precipitating agent is phosphotungstic acid, trichloroacetic acid, ammonium sulfate or a mixture thereof.

29. A method according to claim 28, wherein the relative amount by dry weight of protein-precipitating agent to adsorbing material is about 3:1.

30. A method according to claim 29, wherein about 60–80 mgs of a mixture of about 75% phosphotungstic acid and about 25% silica gel on a dry weight basis is added in step (i).

31. A method according to claim 13, wherein in step (a) the predetermined volume of the whole blood sample is about 50 $\mu$l.

32. A method according to claim 31, wherein in step (e) the predetermined amount of the upper phase is about 0.8 ml.

33. A method according to claim 31, wherein in step (a) the combined volume of alcohol and water added is about 1.5 ml.

34. A method according to claim 33, wherein in step (c) the volume of the added mixture is about 2 ml.

35. A method according to claim 33, wherein in steps (a) and (c) the lower alkyl alcohol is methanol.

36. A method according to claim 13, wherein in step (a) the whole blood sample to be tested is dried onto a support means.

37. A method according to claim 36, wherein the suitable support means is a filter paper strip or circle.

38. A method according to claim 36, wherein in step (a) the addition of the deionized distilled water precedes the addition of the lower alkyl alcohol.

39. A method according to claim 36, wherein the support means onto which the blood is dried has previously been impregnated with a stabilizing agent.

40. A method according to claim 39, wherein the stabilizing agent is selected from the group consisting of a pH 7–8 NaHCO$_3$ solution, a 1% (w/v) sodium azide solution, and a 0.01–1.0% (w/v) benzamidine hydrochloride solution a 0.001–0.01% (w/v) phenylmethylsulfonyl fluoride solution.

41. A cancer diagnostic kit comprising first support means on which the test sample is to be placed; second support means onto which known amounts of reference samples and n-acetyl neuraminic acid standards have been dried; a container of a mixture of chlorinated lower alkyl hydrocarbon and lower alkyl alcohol in a 10:1 volume ratio; a container of a mixture of lower alkyl alcohol and deionized distilled water in a 2:1 volume ratio; a container of protein precipitating agent; a container of resorcinol reagent; a container of a mixture of butyl acetate and n-butanol in an 85:15 volume ratio; a container of deionized distilled water and pipette tips for the sample.

42. A cancer diagnostic kit according to claim 41, wherein the first support means is impregnated with a stabilizing agent.

43. A cancer diagnostic kit comprising first support means comprising paper strips or circles for the sample to be tested; second support means comprising paper strips or circles onto which known amounts of reference samples and n-acetyl neuraminic acid standards have been dried; a container of a mixture of methanol and deionized distilled water in a 2:1 volume ratio; a container of a mixture of chloroform and lower alkyl alcohol in a 10:1 volume ratio; a container of protein precipitating agent; a container of resorcinol reagent; a container of a mixture of butyl acetate and n-butanol in an 85:15 volume ratio; a container of deionized distilled water and pipette tips for the sample.

44. A cancer diagnostic kit according to claim 41 or 43, wherein the protein precipitating agent is in admixture with an adsorbing material.

45. A cancer diagnostic kit according to claim 43, wherein the first support means comprise paper strips or circles which are impregnated with a stabilizing agent.

46. A cancer diagnostic kit according to claim 44, wherein the lower alkyl alcohol is methanol, the precipitating agent is phosphotungstic acid, the adsorbing material is silica gel and the admixture of protein precipitating agent and adsorbing material comprises, 75% phosphotungstic acid and 25% silica gel on a dry weight basis.

* * * * *